US011819459B2

United States Patent
Mosquera et al.

(10) Patent No.: US 11,819,459 B2
(45) Date of Patent: Nov. 21, 2023

(54) METHOD FOR PROVIDING CONTROL DATA FOR AN EYE SURGICAL LASER OF A TREATMENT APPARATUS

(71) Applicant: SCHWIND eye-tech-solutions GmbH, Kleinostheim (DE)

(72) Inventors: Samuel Arba Mosquera, Aschaffenburg (DE); Shwetabh Verma, Aschaffenburg (DE)

(73) Assignee: SCHWIND EYE-TECH-SOLUTIONS GMBH, Kleinostheim (DE)

(*) Notice: Subject to any disclaimer, the term of this patent is extended or adjusted under 35 U.S.C. 154(b) by 3 days.

(21) Appl. No.: 17/487,198

(22) Filed: Sep. 28, 2021

(65) Prior Publication Data

US 2022/0096273 A1 Mar. 31, 2022

(30) Foreign Application Priority Data

Sep. 30, 2020 (DE) ...................... 10 2020 125 552.7

(51) Int. Cl.
*A61F 9/008* (2006.01)

(52) U.S. Cl.
CPC ...... *A61F 9/00804* (2013.01); *A61F 9/00814* (2013.01); *A61F 9/00825* (2013.01); *A61F 2009/0088* (2013.01); *A61F 2009/00882* (2013.01)

(58) Field of Classification Search
CPC .............. A61F 9/00804; A61F 9/00814; A61F 9/00825; A61F 2009/0088; A61F 2009/00882
See application file for complete search history.

(56) References Cited

U.S. PATENT DOCUMENTS

| 8,403,490 | B2 * | 3/2013 | Sugiyama | G02B 26/06 |
| | | | | 359/630 |
| 2012/0249955 | A1 * | 10/2012 | Sarver | A61B 3/10 |
| | | | | 351/246 |

(Continued)

FOREIGN PATENT DOCUMENTS

| DE | 102019107182 A1 | 9/2020 |
| WO | 2017091200 A1 | 6/2017 |

*Primary Examiner* — Michael W Kahelin
*Assistant Examiner* — Naveed R. Kolia
(74) *Attorney, Agent, or Firm* — MEDLER FERRO WOODHOUSE & MILLS PLLC

(57) ABSTRACT

A method for providing control data for an eye surgical laser of a treatment apparatus for removing tissue is disclosed. The method includes utilizing a control device for determining a corneal geometry and an ocular wavefront of a human or animal eye from predetermined examination data. A corneal wavefront is then determined from the corneal geometry using a physical model, and an internal wavefront is calculated from a difference between the ocular wavefront and the corneal wavefront. A wavefront to be achieved is calculated from a difference of a preset target wavefront and the calculated internal wavefront. A target corneal geometry is determined from the wavefront to be achieved by the physical model, and a tissue geometry to be removed is calculated from a difference of the corneal geometry and the target corneal geometry, and control data for controlling the eye surgical laser is provided.

14 Claims, 3 Drawing Sheets

(56) References Cited

U.S. PATENT DOCUMENTS

2016/0150952 A1* 6/2016 Raymond ............ A61B 3/103
                                                  351/205
2020/0297537 A1* 9/2020 Arba-Mosquera ..........................
                                                  A61F 9/00804

* cited by examiner

METHOD FOR PROVIDING CONTROL DATA FOR AN EYE SURGICAL LASER OF A TREATMENT APPARATUS

The present invention relates to a method for providing control data for an eye surgical laser of a treatment apparatus for removing tissue. In addition, the invention relates to a treatment apparatus with at least one eye surgical laser for removing tissue of a human or animal eye by means of photodisruption and/or photoablation, and at least one control device for performing the method, to a computer program and to a computer-readable medium.

Treatment apparatuses and methods for controlling ophthalmologic lasers for correcting a visual disorder and/or pathologically and/or unnaturally altered areas of the cornea are known in the prior art. Therein, a pulsed laser and a beam focusing device can for example be formed such that laser beam pulses effect photodisruption and/or photoablation in a focus located within organic tissue to remove the tissue, in particular a lenticule, from the cornea.

For determining a tissue geometry of the tissue to be removed to for example correct an optical visual disorder, various approaches are known. Therein, in one of these approaches, a ray path through the eye is simulated via ray tracing on a computer model, wherein a cornea to be achieved is iteratively calculated for determining the tissue geometry. It is disadvantageous in this method that a high computing power and long computing times are required for this iterative process and that the calculations are only based on a model of the eye, wherein assumptions from the literature about the shape of the lens, the retina radius, the refractive indices and their distribution in the lens are assumed hereto. Furthermore, an adaptation load by the treatment is usually completely on a front side of the lens.

The invention is based on the object to provide control data for controlling an eye surgical laser with a tissue geometry determined in improved manner for removing tissue.

This object is solved by the method according to the invention, the apparatuses according to the invention, the computer program according to the invention as well as the computer-readable medium according to the invention. Advantageous configurations with convenient developments of the invention are specified in the respective dependent claims, wherein advantageous configurations of the method are to be regarded as advantageous configurations of the treatment apparatus, of the control device, of the computer program and of the computer-readable medium and vice versa.

A first aspect of the invention relates to a method for providing control data for an eye surgical laser of a treatment apparatus for removing tissue, wherein the method comprises the following steps performed by a control device. Therein, an appliance, an appliance component or an appliance group is understood by a control device, which is configured for receiving and evaluating signals, as well as for providing, for example generating, control data. For example, the control device can be configured as a control chip, computer program, computer program product or control unit. Ascertaining a corneal geometry of a cornea of a human or animal eye from predetermined examination data, ascertaining a corneal wavefront by means of a physical model from the corneal geometry, wherein a change of an input wavefront upon a passage through the cornea with the ascertained corneal geometry is determined for ascertaining the corneal wavefront by means of the physical model, and ascertaining an ocular wavefront of the human or animal eye from the predetermined examination data, wherein a change of the input wavefront upon passage through the entire human or animal eye is described by the ocular wavefront, are effected by the control device. Subsequently, calculating an internal wavefront from a difference of the ocular wavefront and the corneal wavefront, calculating a wavefront to be achieved from a difference of a preset target wavefront and the calculated internal wavefront and ascertaining a target corneal geometry from the wavefront to be achieved by means of the physical model are effected by the control device, wherein the target corneal geometry, which results in the wavefront to be achieved upon a passage of the input wavefront through a target cornea with the target corneal geometry, is described by means of the physical model. Finally, calculating a tissue geometry to be removed from a difference of the corneal geometry and the target corneal geometry and providing control data for controlling the eye surgical laser, which includes the tissue geometry to be removed for removing the tissue, are effected by the control device.

In other words, a corneal geometry and an ocular wavefront of the eye are first ascertained from predetermined examination data, wherein a topography and/or a wavefront analysis can for example be performed hereto. Subsequently, a corneal wavefront can be determined by means of a physical model and the corneal geometry, wherein the corneal wavefront can be determined from an analytical calculation, which an input wavefront passes upon a passage through the cornea with the ascertained corneal geometry. That means that the corneal wavefront results by a change of the input wavefront when the input wavefront is changed by the cornea with the ascertained corneal geometry. Herein, the physical model can be based on physical laws of reflection and refraction and describe a geometric change of the respective rays of the wavefront. Subsequently, an internal wavefront can be calculated from the ascertained ocular wavefront, which represents a change of the input wavefront after a passage through the entire eye, and the corneal wavefront ascertained by the physical model. This internal wavefront can preferably be determined from a difference of the ocular wavefront and the corneal wavefront.

Herein, the internal wavefront, which can be used as an intermediate step for calculating the tissue geometry to be removed, describes light refraction, which arises by all of the components less the cornea. In particular, the internal wavefront describes light refraction by a lens of the eye and a vitreous body of the eye, in particular of an aqueous humor of the vitreous body. As a next step, this calculated internal wavefront can be subtracted from a preset target wavefront to obtain a wavefront to be achieved. Therein, the preset target wavefront represents the wavefront, which finally is to be incident on the retina of the eye, and the wavefront to be achieved is that wavefront, which is to be achieved by the treatment of the cornea. This means that the input wavefront is to be changed by the treatment of the cornea such that the input wavefront becomes the wavefront to be achieved after the cornea and the input wavefront to be achieved becomes the preset target wavefront incident on the retina after passage through the remaining eye, in particular the lens and the vitreous body.

A target corneal geometry, which changes the input wavefront into the wavefront to be achieved, can then be determined from the wavefront to be achieved from a back-calculation by means of the physical model. In other words, it is analytically determined, which target corneal geometry changes the input wavefront to the wavefront to be achieved.

Finally, a tissue geometry to be removed can be calculated by means of the target corneal geometry and the initially determined corneal geometry. Therein, the tissue geometry to be removed describes the tissue, which has to be removed from the corneal geometry to arrive at the target corneal geometry. The thus calculated tissue geometry to be removed can then be provided as control data to the eye surgical laser for removing the tissue.

For performing the method, the respective wavefronts can be present as a wavefront map, wherein a wavefront map is a color-coded representation of a wavefront deformation as a function of the location within the eye, in particular within the pupil. The corneal geometry, the target corneal geometry and the tissue geometry have respective dimensions and shapes of the cornea, in particular a volume, a shape, a thickness, a diameter and/or a position.

By this aspect of the invention, the advantage arises that the tissue geometry to be removed can be simply and fast determined. In particular, a high individualization for the treatment of the eye can be achieved, wherein the ocular and corneal wavefront of the patient can be directly taken into account, and it does not have to be resorted to literature values. By the improved and individualized determination of the tissue geometry to be removed, a reduction of the tissue to be removed can in particular also be achieved. Compared to known approaches, there is the advantage that the determination of the tissue to be removed can be directly performed on measured predetermined examination data, whereby errors, in particular errors due to error propagation, can be reduced. Furthermore, computing power and/or computing time can be saved by an analytical calculation since the method is not based on an iterative calculation in contrast to previous ray tracing approaches.

The invention also includes forms of configuration, by which further advantages arise.

According to an advantageous form of configuration, it is provided that a ray modeling according to the Fermat's principle is used for the physical model. The Fermat's principle indicates that light in a medium takes that path between two points, on which its transit time is shortest. In particular, the law of reflection and the Snell's law of refraction can be derived from the Fermat's principle. By means of the Fermat's principle, a respective ray of the respective wavefront can be analytically calculated by means of the ascertained geometry, in particular the corneal geometry, in the method, since all of the parameters required thereto are present from the predetermined examination data. By this embodiment, the advantage arises that the tissue geometry to be removed can be fast and simply determined, wherein this determination can be analytically performed based on the Fermat's principle, which saves computing time and/or computing power compared to iterative approaches.

According to a further advantageous form of configuration, it is provided that a plane wave is used as the input wavefront for ascertaining the corneal wavefront, wherein the input wavefront extends perpendicularly to an optical axis of the cornea, wherein the corneal wavefront is calculated according to the formula:

$$CW=-(TQ+n(QF-OF))$$

wherein CW is the corneal wavefront, wherein TQ is a distance of a respective ray of the input wavefront up to the cornea with the ascertained corneal geometry, wherein n is a refractive index of the cornea, wherein OF is a medium focal length of the cornea up to a focal point F and wherein QF is a distance from a position, in which the respective ray of the input wavefront TQ is incident on the cornea, up to the focal point F. In particular, the above mentioned formula represents a possibility of analytically calculating the corneal wavefront, wherein computing power can be advantageously saved hereby compared to iterative methods. A further explanation of the formula is effected later in the description of figures, in particular in context of FIG. 4.

According to a further advantageous form of configuration, it is provided that the target corneal geometry is ascertained from the wavefront to be achieved by means of a back-calculation, wherein the back-calculation is performed according to the Fermat's principle. In other words, by suitable rearrangement of the above mentioned formula, it is calculated, which target corneal geometry is required to obtain the wavefront to be achieved. It is the advantage of this form of configuration that the back-calculated target corneal geometry can be analytically determined, which saves computing power and/or computing time.

Preferably, it is provided that the predetermined examination data for the corneal geometry is measured by means of corneal topography. In other words, the corneal geometry is for example determined by means of a keratograph, by means of which a curvature of the cornea, a corneal thickness, in particular height data, and a refractive power of the cornea can be determined. Preferably, it is provided that the predetermined examination data for the ocular wavefront is measured by means of aberrometry. The aberrometry, which can also be referred to as wavefront analysis and which can for example be performed by a Hartmann-Shack sensor, can describe a change of an input wavefront upon passage through the entire eye. Hereto, the ocular wavefront can in particular be described by means of Zernike polynomials. Particularly preferably, it is provided that the predetermined examination data, that is both the corneal geometry and the ocular wavefront, is measured by means of a single examination apparatus to minimize errors.

According to a further advantageous form of configuration, it is provided that a shape of the target wavefront is preset by a curvature shape of a retina of the human or animal eye. In other words, it can be provided that the target wavefront, thus that wavefront, which finally is incident on the retina, has a shape, which is adapted to the retina. In particular, the target wavefront can be curved in the same manner as the retina. Hereby, the advantage arises that an optimum visual disorder correction can be preset for the eye. However, other shapes can also be preset for the target wavefront, for example a plane target wavefront or another desired shape, which can be preset by a user of the treatment apparatus.

A second aspect of the present invention relates to a control device, which is configured to perform one of the above described methods. The advantages cited above arise. The control device can for example be configured as a control chip, control unit or application program ("app"). The control device can preferably comprise a processor device and/or a data storage. An appliance or an appliance component for electronic data processing is understood by a processor device. The processor device can for example comprise at least one microcontroller and/or at least one microprocessor. Preferably, a program code for performing the method according to the invention can be stored on the optional data storage. Then, the program code can be configured, upon execution by the processor device, to cause the control device to perform one of the above described embodiments of one or both methods according to the invention.

A third aspect of the present invention relates to a treatment apparatus with at least one eye surgical laser for the separation of a tissue predefined by the control data, in particular of a corneal volume with predefined interfaces of a human or animal eye, by means of photodisruption and/or photoablation, and at least one control device for the laser or lasers, which is formed to execute the steps of the method according to the first aspect of the invention. The treatment apparatus according to the invention allows that the disadvantages occurring in the use of usual ablative treatment apparatuses are reliably reduced or even avoided.

In a further advantageous configuration of the treatment apparatus according to the invention, the laser can be suitable to emit laser pulses in a wavelength range between 300 nm and 1400 nm, preferably between 700 nm and 1200 nm, at a respective pulse duration between 1 fs and 1 ns, preferably between 10 fs and 10 ps, and a repetition frequency of greater than 10 kilohertz (kHz), preferably between 100 kHz and 100 megahertz (MHz). Such a femtosecond laser is particularly well suitable for removing tissue within the cornea. The use of photodisruptive and/or photoablative lasers in the method according to the invention additionally has the advantage that the irradiation of the cornea does not have to be effected in a wavelength range below 300 nm. In the laser technology, this range is subsumed by the term "deep ultraviolet". Thereby, it is advantageously avoided that an unintended damage to the cornea is caused by these very short-wavelength and high-energy beams. Photodisruptive lasers of the type used here usually input pulsed laser radiation with a pulse duration between 1 fs and 1 ns into the corneal tissue. Thereby, the power density of the respective laser pulse required for the optical breakthrough can be spatially narrowly limited such that a high incision accuracy in the generation of the interfaces is allowed. In particular, the range between 700 nm and 780 nm can also be selected as the wavelength range.

In further advantageous configurations of the treatment apparatus according to the invention, the control device can comprise at least one storage device for at least temporary storage of at least one control dataset, wherein the control dataset or datasets include(s) control data for positioning and/or for focusing individual laser pulses in the cornea; and can comprise at least one beam device for beam guidance and/or beam shaping and/or beam deflection and/or beam focusing of a laser beam of the laser. Therein, the mentioned control dataset includes the control data determined in the method for removing the tissue.

Further features and the advantages thereof can be taken from the descriptions of the first inventive aspect, wherein advantageous configurations of each inventive aspect are to be regarded as advantageous configurations of the respectively other inventive aspect.

A fourth aspect of the invention relates to a computer program including instructions, which cause the treatment apparatus according to the third inventive aspect to execute the method steps according to the first inventive aspect and/or the method steps according to the second inventive aspect.

A fifth aspect of the invention relates to a computer-readable medium, on which the computer program according to the fourth inventive aspect is stored. Further features and the advantages thereof can be taken from the descriptions of the first to fourth inventive aspects, wherein advantageous configurations of each inventive aspect are to be regarded as advantageous configurations of the respectively other inventive aspect.

Further features are apparent from the claims, the figures and the description of figures. The features and feature combinations mentioned above in the description as well as the features and feature combinations mentioned below in the description of figures and/or shown in the figures alone are usable not only in the respectively specified combination, but also in other combinations without departing from the scope of the invention. Thus, implementations are also to be considered as encompassed and disclosed by the invention, which are not explicitly shown in the figures and explained, but arise from and can be generated by separated feature combinations from the explained implementations. Implementations and feature combinations are also to be considered as disclosed, which thus do not comprise all of the features of an originally formulated independent claim. Moreover, implementations and feature combinations are to be considered as disclosed, in particular by the implementations set out above, which extend beyond or deviate from the feature combinations set out in the relations of the claims.

In the figures, identical or functionally identical elements are provided with the same reference characters.

Figure 1:
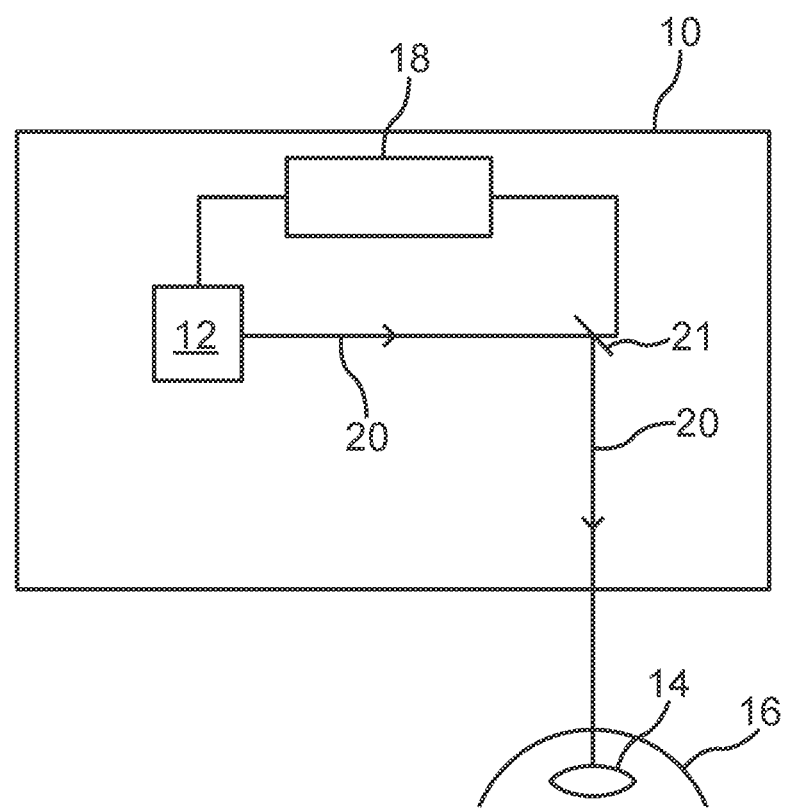
FIG. 1 is a schematic representation of a treatment apparatus according to an exemplary embodiment.

FIG. 1 shows a schematic representation of a treatment apparatus 10 with an eye surgical laser 12 for removing tissue 14 of a human or animal eye 16 by means of photodisruption and/or photoablation. For example, the tissue 14 can represent a lenticule or also volume body, which can be separated out of a cornea of the eye 16 by the eye surgical laser 12 for correcting a visual disorder. A geometry of the tissue 14 to be removed can be provided by a control device 18, in particular in the form of control data, such that the laser 12 emits pulsed laser pulses in a pattern predefined by the control data into the cornea of the eye 16 to remove the tissue 14. Alternatively, the control device 18 can be a control device 18 external with respect to the treatment apparatus 10.

Furthermore, FIG. 1 shows that the laser beam 20 generated by the laser 12 can be deflected towards the eye 16 by means of a beam device 21, namely a beam deflection device such as for example a rotation scanner, to remove the tissue 14. The beam deflection device 21 can also be controlled by the control device 18 to remove the tissue 14.

Preferably, the illustrated laser 12 can be a photodisruptive and/or photoablative laser, which is formed to emit laser pulses in a wavelength range between 300 nanometers and 1400 nanometers, preferably between 700 nanometers and 1200 nanometers, at a respective pulse duration between 1 femtosecond and 1 nanosecond, preferably between 10 femtoseconds and 10 picoseconds, and a repetition frequency of greater than 10 kilohertz, preferably between 100 kilohertz and 100 megahertz. In addition, the control device 18 optionally comprises a storage device (not illustrated) for at least temporary storage of at least one control dataset, wherein the control dataset or datasets include(s) control data for positioning and/or for focusing individual laser pulses in the cornea. The position data and/or the focusing data of the individual laser pulses, that is the geometry of the tissue 14, are ascertained based on the method described below.

Figure 2:
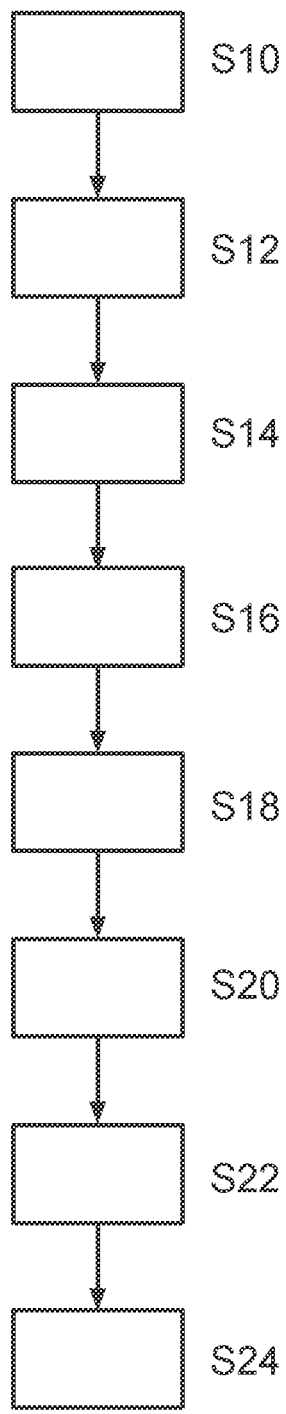
FIG. 2 is a schematic method diagram according to an exemplary embodiment.
Figure 3:
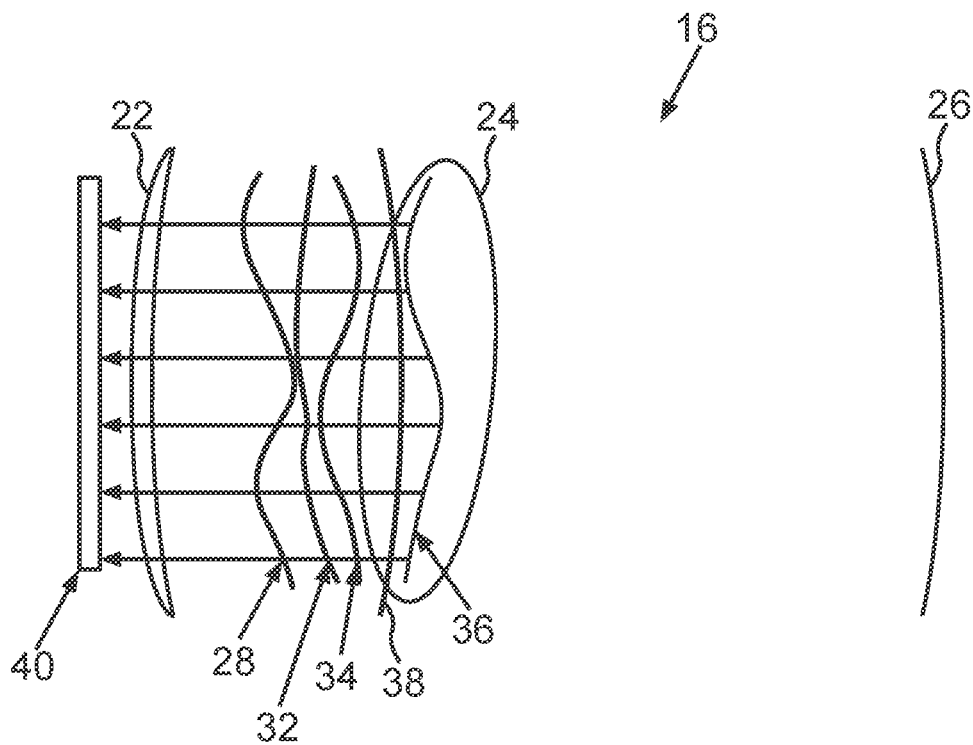
FIG. 3 is a cross-section through a schematically illustrated eye with wavefronts for calculating a tissue geometry to be removed.

In particular, the control device 18 can perform the method, which is represented according to an exemplary embodiment in FIG. 2, for providing control data. For explaining the method steps, reference is also made to FIG. 3, in which a side view of a schematically illustrated eye 16 is shown, with respective wavefronts, which are ascertained in the method. Therein, the eye 16 illustrated in FIG. 3 can include a cornea 22, a lens 24 and a retina 26.

In a step S10 of the method, a corneal geometry of the cornea 22 of the eye 16 is ascertained from predetermined examination data. The corneal geometry can for example have been measured by means of corneal topography.

In a step S12, a corneal wavefront 28 can then be determined from the corneal geometry of the cornea 22 by means of a physical model. The physical model can describe a change of an input wavefront (not illustrated in FIG. 3) upon a passage through the cornea 22, wherein the input wavefront becomes the corneal wavefront 28 after passage through the cornea 22. Preferably, the physical model can be based on the Fermat's principle, which indicates in simplified manner that light takes the fastest and not the shortest path. For accurately calculating the corneal wavefront 28, the formula:

$$CW=-(TQ+n(QF-OF))$$

can for example be used, wherein a plane wave is here assumed as the input wavefront, which is incident on the cornea 22. In the following, the above mentioned formula is explained in more detail based on FIG. 4.

Figure 4:
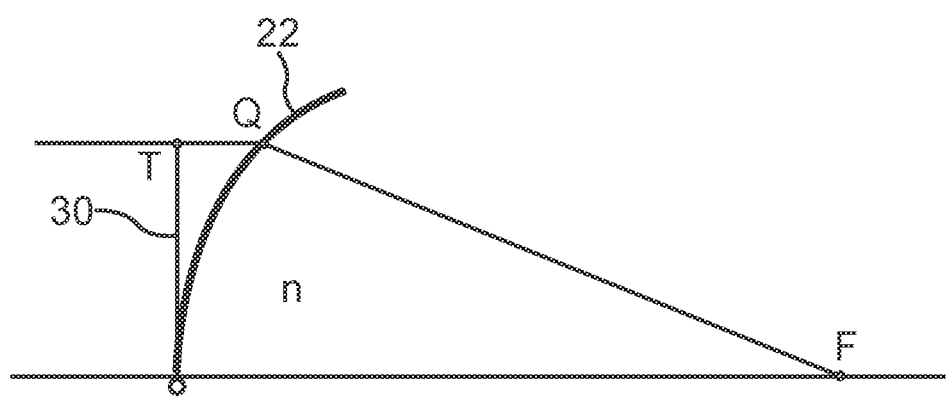
FIG. 4 is a schematic representation of ray paths for ascertaining a corneal wavefront.

In FIG. 4, ray paths for determining the corneal wavefront 28 according to the Fermat's principle are exemplarily illustrated. A plane input wavefront 30 is illustrated, which is incident on the cornea 22, in particular on the point O of the cornea 22, which can be located on an optical axis of the eye 16. Therein, for deriving the above indicated formula, it is assumed according to the Fermat's principle that a ray of the plane wave 30 on the distance from T to Q in air and additionally from the point Q to the point F in the cornea with the refractive index n has a same optical path length compared to a ray of the plane wave 30 from the point O to the point F, wherein the point F represents a focal point of a medium focal length of the cornea 22. A continuation of this assumption then results in the above mentioned formula, wherein TQ represents the distance from the point T to the point Q, the distance QF represents a distance from the point Q to the medium focal point F and the distance OF represents a distance from the point O to the medium focal point F. The value n is a refractive index of the cornea 22. Accordingly, a change of the input wavefront to the corneal wavefront can be calculated from the ascertained corneal geometry, which is taken into account in the distance TQ.

After determining the corneal wavefront 28, an ocular wavefront 32 can be ascertained from the predetermined examination data in a step S14, wherein the ocular wavefront 32 represents a change of the input wavefront 30 upon a passage through the entire eye 16. The ocular wavefront 32 can be determined from a measurement by means of aberrometry (wavefront analysis) for the entire eye 16. Preferably, the examination data, in particular the corneal geometry and the ocular wavefront, can be measured with a single examination apparatus to minimize measurement errors in the determination of the examination data.

In a step S16, an internal wavefront 34 can then be calculated from a difference of the ocular wavefront 32 and the corneal wavefront 28. Therein, the internal wavefront represents a change of the wavefront by the lens 24 and further components of the eye 16, such as for example a vitreous body with an aqueous humor. In particular, the internal wavefront 34 is calculated by a difference of the ocular wavefront 32, which describes a change of an input wavefront by the entire eye, and the corneal wavefront, which describes a change by the cornea 22.

In a further step S18, a wavefront 36 to be achieved is determined from a difference of a preset target wavefront 38 and the calculated internal wavefront 34. For example, the target wavefront 38 can be preset by a user, for example a physician, and specify how the wavefront is to look like, which is incident on the retina 26. Preferably, the target wavefront 38 can be preset such that a curvature shape of the target wavefront 38 corresponds to a curvature shape of the retina 26. However, the target wavefront can also be preset as a plane wave or with another geometry. Therein, the wavefront 36 to be achieved represents that wavefront, which is required to arrive at the preset target wavefront 38 after a passage through the lens 24 up to the retina 26. In other words, the wavefront 36 to be achieved is diffracted by the lens 24 and further components such that the target wavefront 38 results. In order to calculate the wavefront 36 to be achieved, the calculated internal wavefront 34 is subtracted from the preset target wavefront 38.

Subsequently, a target corneal geometry 40 can be ascertained from the wavefront 36 to be achieved by means of the physical model, preferably by means of the physical model according to the Fermat's principle, in a step S20. Herein, it is back-calculated how the target corneal geometry 40 would have to look like, which changes the input wavefront 30 to the wavefront 36 to be achieved. A back-calculation according to the Fermat's principle can suitably be derived from the above mentioned formula and from FIG. 4.

Subsequently, a tissue geometry to be removed (not shown) can be calculated from a difference of the corneal geometry of the cornea 22 and the target corneal geometry 40 in a step S22. This means that the tissue geometry to be removed represents the geometry, which has to be removed from the cornea 22 to arrive at a cornea with the target corneal geometry.

In a step S24, control data for controlling the eye surgical laser 12 can finally be provided, wherein the control data uses the tissue geometry to be removed for removing the tissue 14.

Overall, the examples show how a calculation of a pseudo ray tracing based on corneal, ocular and refractive information can be performed by the invention.

What is claimed is:

1. A method for controlling an eye surgical laser of a treatment apparatus for removing tissue, wherein the method comprises the following steps performed by a control device:

ascertaining a corneal geometry of a cornea of a human or animal eye from predetermined examination data;

ascertaining a corneal wavefront from the corneal geometry using a physical model, wherein a change of an input wavefront upon a passage through the cornea with the ascertained corneal geometry is determined for ascertaining the corneal wavefront using the physical model, wherein the physical model is based on physical laws of reflection and refraction and describes a geometric change of respective rays of the input wavefront;

ascertaining an ocular wavefront of the human or animal eye from the predetermined examination data, wherein a change of the input wavefront upon a passage through the entire human or animal eye is described by the ocular wavefront;

calculating an internal wavefront from a difference of the ocular wavefront and the corneal wavefront;

calculating a wavefront to be achieved from a difference of a preset target wavefront and the calculated internal wavefront;

ascertaining a target corneal geometry from the wavefront to be achieved using the physical model, wherein the target corneal geometry is determined using the physical model, which results in the wavefront to be achieved upon a passage of the input wavefront through a target cornea with the target corneal geometry;

calculating a tissue geometry to be removed from a difference of the corneal geometry and the target corneal geometry;

providing control data for controlling the eye surgical laser, which includes the tissue geometry to be removed for removing the tissue; and controlling the eye surgical laser by the provided control data.

2. The method according to claim 1, wherein beam modelling according to Fermat's principle is used for the physical model.

3. The method according to claim 2, wherein for ascertaining the corneal wavefront, a plane wave is used as the input wavefront, wherein the input wavefront extends perpendicularly to an optical axis of the cornea, wherein the corneal wavefront is calculated according to the formula $CW=-(TQ+n(QF-OF))$, wherein CW is the corneal wavefront wherein TQ is a distance of a respective ray of the input wavefront up to the cornea with the ascertained corneal geometry, wherein n is a refractive index of the cornea, wherein OF is a medium focal length of the cornea up to a focal point F, and wherein QF is a distance from a position, in which the respective ray of the input wavefront TQ is incident on the cornea, up to the focal point F.

4. The method according to claim 1, wherein the target corneal geometry is ascertained using back-calculation from the wavefront to be achieved, wherein the back-calculation is performed according to Fermat's principle.

5. The method according to claim 1, wherein the predetermined examination data for the corneal geometry is measured using corneal topography.

6. The method according to claim 1, wherein the predetermined examination data for the ocular wavefront is measured using aberrometry.

7. The method according to claim 1, wherein a shape of the target wavefront is preset by a curvature shape of a retina of the human or animal eye.

8. A control device, which is configured to perform a method according to claim 1.

9. A treatment apparatus with at least one eye surgical laser for removing tissue of a human or animal eye, in particular a lenticule, using photodisruption and/or photoablation, and at least one control device according to claim 8.

10. The treatment apparatus according to claim 9, wherein the laser is formed to emit laser pulses in a wavelength range between 300 nm and 1400 nm at a respective pulse duration between 1 fs and 1 ns and a repetition frequency of greater than 10 kHz.

11. The treatment apparatus according claim 9, wherein the control device comprises at least one storage device for at least temporary storage of at least one control dataset, wherein the control dataset or datasets include(s) control data for positioning and/or focusing individual laser pulses in the cornea; and includes at least one beam device for beam guidance and/or beam shaping and/or beam deflection and/or beam focusing of a laser beam of the laser.

12. A computer program including instructions that cause a treatment apparatus having at least one eye surgical laser for removing tissue of a human or animal eye, in particular a lenticule, using photodisruption and/or photoablation, and at least one control device, to execute a method according to claim 1.

13. A non-transitory computer-readable medium, on which the computer program according to claim 12 is stored.

14. The treatment apparatus according to claim 10, wherein the wavelength range is between 700 nm and 1200 nm, at a respective pulse duration between 10 fs and 10 ps, and the repetition frequency is between 100 kHz and 100 MHz.

* * * * *